(12) United States Patent
Navelier et al.

(10) Patent No.: US 6,623,446 B1
(45) Date of Patent: Sep. 23, 2003

(54) NEEDLELESS SYRINGE COMPRISING AN INJECTOR WITH STACKED ELEMENTS

(75) Inventors: Alain Navelier, Pierrefeu du Var (FR); Patrick Alexandre, Gray (FR); Bernard Brouquieres, Toulon (FR); Denis Roller, La Ferte Alais (FR)

(73) Assignee: Crossject, Paris (FR)

( * ) Notice: Subject to any disclaimer, the term of this patent is extended or adjusted under 35 U.S.C. 154(b) by 0 days.

(21) Appl. No.: 10/018,223

(22) PCT Filed: Jun. 30, 2000

(86) PCT No.: PCT/FR00/01850

§ 371 (c)(1),
(2), (4) Date: Dec. 18, 2001

(87) PCT Pub. No.: WO01/05453

PCT Pub. Date: Jan. 25, 2001

(30) Foreign Application Priority Data

Jul. 16, 1999 (FR) .............................. 99 09253

(51) Int. Cl.[7] .............................................. A61M 5/30
(52) U.S. Cl. .............................. 604/68; 604/69; 604/70
(58) Field of Search .................. 604/176, 236, 604/68, 70, 143, 72–75, 71, 110, 135, 187

(56) References Cited

U.S. PATENT DOCUMENTS 3,788,315 A 1/1974 Laurens
4,722,728 A * 2/1988 Dixon ........................ 604/68
5,074,843 A 12/1991 Dalto et al.
5,334,144 A * 8/1994 Alchas et al. ................. 604/68

FOREIGN PATENT DOCUMENTS

DE 196 07 922 A1 9/1997
FR 1 378 829 A 2/1965

OTHER PUBLICATIONS

Bellhouse et al. partical delivery, Jan. 10, 2002, US Publication No. US 2002/0004641.*

* cited by examiner

Primary Examiner—Michael J. Hayes
Assistant Examiner—Roz Ghafoorian
(74) Attorney, Agent, or Firm—Oliff & Berridge, PLC

(57) ABSTRACT

The invention concerns the technical field of needleless syringes for injecting an active principle for therapeutic purposes. More particularly, it concerns a needleless syringe for injecting an active principle (7, 70) initially set between an injector (1, 10) comprising at least an injection nozzle (50, 50', 60') contacted with the skin and a wall (8) mobile under the effect of a propelling system (9) pressurizing and expelling the active principle through the injector located at the downstream end (2, 20) of the syringe. In order to produce nozzles passing through a considerable injector thickness and to control the jet coherence distance, said injector (1, 10) comprises a support (3, 21) with at least a housing (4, 40) wherein are stacked plates (51, 61, 91, 51', 71', 91', 52, 92) each comprising an equal number of orifices aligned to form at least a nozzle (50, 50', 60') through the stack.

8 Claims, 2 Drawing Sheets

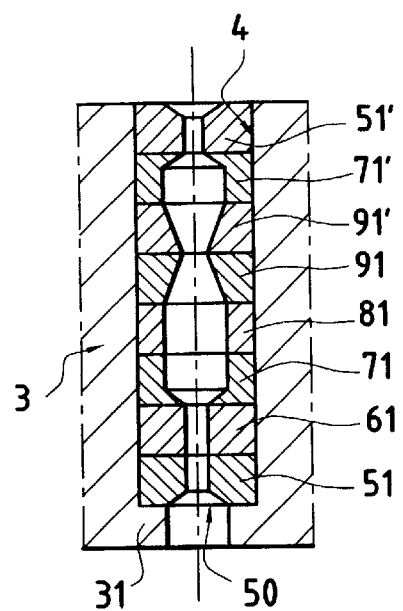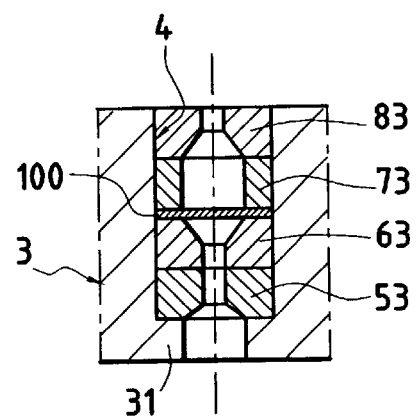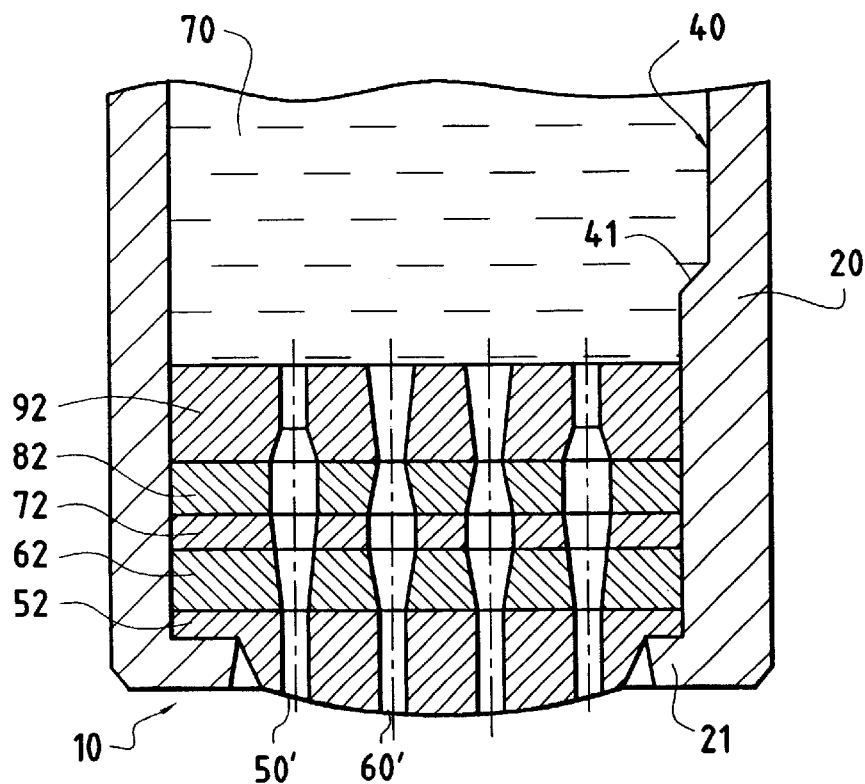

NEEDLELESS SYRINGE COMPRISING AN INJECTOR WITH STACKED ELEMENTS

The present invention is in the field of needleless syringes used for intradermic, subcutaneous and intramuscular injections of liquid active principle for therapeutic use in human or veterinary medicine In this field, to improve the effectiveness of the injection, use is made of syringes with, at their downstream part applied to the skin or very close to skin of the subject, an injector comprising several ducts so that the liquid that is to be injected can be distributed to several points spread over a relatively large area. This solution also has the advantage of reducing the pain and eliminating any possible superficial or subcutaneous damage that might result from an excessive amount of liquid injected at a single point.

To improve the effectiveness of the injection, the shape of the jet is also altered: the coherence distance of the jet is controlled and a solution is sought that is some way between a highly coherence jet, such as used for jet cutting and which would have very deep penetration and would cause dangerous tearing of the skin, and a jet which nebulizes the liquid and whose fine droplets do not penetrate the skin.

U.S. Pat. No. 3,802,430 describes a needleless syringe in which the liquid that is to be injected is discharged by a piston pushed by gases produced by a pyrotechnic generator; that syringe has five ducts which are parallel to the axis of the syringe and have circular cross sections. U.S. Pat. No. 3,788,315 describes a syringe in which the piston discharging the liquid is pushed by the expansion of compressed gases or of a compressed spring. That syringe has six ducts of circular cross sections and the axes of which diverge slightly from the axis of the syringe. In these examples, although the liquid is spread across several points, the ducts remain fairly close together; in addition, the simplicity of the shape of these ducts shows that these ducts are not optimized for controlling the coherence length of the jet which is itself an important factor in the performance of the injector in this particular application.

More generally, the problems posed by producing an injector for a syringe are problems of mechanical strength, of performance as we have just mentioned, and of cost.

Specifically, the injector, placed at the downstream part of the syringe, must not deform under the effect of the pressure of the liquid at the time of injection: the injector has to be relatively thick, and the more widely the ducts are spread over a large area, the thicker it has to be. The problem will be that of producing ducts which in general are very fine through great thicknesses.

The performance of the injector lies in the possibility of controlling the coherence distance of the jets leaving the ducts or nozzles, for predetermined conditions of use (nature of the liquid, injection pressure), through ducts of appropriate cross sections. The purpose of this appropriate cross section is to create a field of turbulence in the flow such that, a short distance from the exit from the injector, the jet remains coherence, that is to say is fine and fast-moving enough to pierce and penetrate the skin of the subject that is to be treated, and then the jet very quickly loses its coherency: it explodes to best diffuse the active principle under the skin. The problem is that of, in a simple way, producing not only fine ducts through great thicknesses but, above all, ducts with appropriate cross sections.

Finally, the cost of manufacture becomes a very important factor in the case of mass-produced syringes, particularly for disposable syringes.

The present invention relates to a needleless syringe for intradermic, subcutaneous or intramuscular injecting of a liquid active principle initially placed between, on the one hand, an injector comprising at least one injection nozzle or duct, the said injector being placed in contact with the skin or very close to the skin of the subject that is to be treated, and, on the other hand, a wall that can be displaced under the effect of a propulsive system which pressurizes and expels the active principle through the injector placed at the downstream end of the syringe, and such that the said injector comprises a support with at least one housing in which plates each having the same number of orifices are stacked, the said orifices of the various plates being aligned to form at least one nozzle through the stack. More specifically, each orifice of each plate is aligned with a corresponding orifice of an adjacent plate, the succession of the orifices of the various plates forming an injection nozzle.

In this invention, "liquid active principle" is essentially intended to mean a somewhat viscous liquid, or a mixture of liquids, or a gel. The active principle may be a solid placed in solution in an appropriate solvent for injection. The active principle may be a solid in pulverulent form placed in suspension, of greater or lesser concentration, in an appropriate liquid. The particle size of the solid active principle and the shape of the duct need to be matched to avoid the ducts becoming blocked.

The plates have simple geometric shapes, for example polygonal, elliptical or circular shapes. The housings in the support, in which housings the said plates are stacked, naturally have mating shapes which allow the plates to be fitted in. These plates are generally planar, with parallel faces for greater simplicity; however, in the case of certain plates, at least one face may be convex or concave. Finally, these plates may or may not have equal thicknesses.

Orifices in a plate are holes through the plate. These holes either have symmetry of revolution: circular cross section, or do not have such symmetry: polygonal (triangular, square, etc) cross section or hybrid cross section (that is to say a cross section with some non-straight sides). Grooves made along the edge of a plate will be likened to holes. The various plates are stacked in a housing in such a way that the holes or grooves in each plate follow on from one another to form nozzles through the stack.

In one particular embodiment, the needleless syringe is such that the said injector comprises a support with a single housing in which plates each having the same number of orifices are stacked, the said orifices being aligned to form at least one nozzle through the stack.

As a preference, the orifices corresponding to one another in the plates have different geometric shapes so as, through their succession in the stack, to produce nozzles of evolving cross section. This evolving cross section is obtained by combining, within the stack, orifices of different shaped cross sections; for example, cylindrical or frustoconical orifices, or orifices with curved profiles, or a succession of ducts and cavities for producing a nozzle with an evolving cross section.

Advantageously, the plates comprise means of setting the angle of the said plates in the corresponding housing, in such a way that the orifices correspond to one another and follow on from one another to produce a nozzle with evolving cross section. The setting of the angle is achieved through mating shapes of the housing and of the plates if they have polygonal shapes. If the housings have shapes which have symmetry of revolution, angular setting will be achieved by a pin passing through all the plates and arranged to the side or by a rib in the housing engaging in a notch in the plates or by any other equivalent device.

As a preference, the shapes of the housings and of the plates are such that, during injection, the pressure of the liquid locks the plates against a shoulder of the housing, or locks them through an appropriate taper: a portion of smaller cross section toward the downstream end.

In a first embodiment of the syringe, at least the most downstream plate is forcibly fitted into a housing to ensure leaktightness.

In a second embodiment of the syringe, at least the most downstream plate is bonded into its housing. Advantageously, the support for the plates is the downstream end of the syringe itself. This downstream end is configured, with a shoulder or a taper, to accommodate the stack of plates.

In an alternative form of the syringe according to the invention, the said injector comprises at least one plate constitution a crossable membrane inserted between two consecutive plates.

In the absence of pressure, this crossable membrane blocks off the nozzle formed by the aligned orifices of the stacked plates: the membrane thus prevents losses of liquid as a result of shaking or rough handling of the syringe. At the time of injection, the liquid is pressurized by the moveable wall activated by the propulsive system, and the liquid will cross the said membrane.

In a first embodiment, the membrane is quite thin so that it can be pierced, opposite the injection nozzles or ducts, when the liquid is placed at high pressure in order to perform the injection.

In a second embodiment, the membrane has a region of lesser thickness facing each injection duct; each of these regions is pierced, as before, at the time of pressurizing. For correct operation in this embodiment, the membrane needs to be correctly positioned, by appropriate devices, so that each region of lesser thickness faces an injection duct. A region of lesser thickness is a blind cavity formed in the membrane. One of the simplest forms is that of a cone or cone frustum.

In a third embodiment, the membrane comprises a prepiercing facing each injection duct. The elasticity of the elastomer of the membrane keeps each of the pre-piercings closed and this closure may possibly be leaktight. When the liquid is pressurized by the triggering of the propulsive system, each pre-piercing opens.

The present invention relates also to an injector for a needleless syringe. The said injector comprises a support with at least one housing in which plates each having the same number of orifices are stacked, the said orifices being aligned to form at least one nozzle through the stack.

Finally, the present invention relates to a method of manufacturing an injector for a needleless syringe. This method comprises the following steps:
  manufacturing a support comprising at least one housing,
  manufacturing plates all having the same number of orifices, of appropriately chosen geometries,
  stacking and setting the plates in a predetermined order in each housing to form at least one nozzle through the stack.

A syringe according to the invention solves the problems posed. In terms of the strength of the injector, the increase in the thickness poses no difficulty with respect to the production of fine ducts, with evolving or non-evolving cross sections, through great thicknesses.

The invention makes it possible, in a simple way, in order to suit the predetermined conditions of use, to control the coherence distance of the jets leaving the nozzles.

As far as the cost aspect is concerned, the injector comprises elements of simple shapes which are easy to produce, these elements are also simple to assemble and above all lend themselves well to a high degree of automation.

The syringe according to the invention additionally has an undeniable advantage from the point of view of safety in the event of abnormal use. For example, if the syringe is aimed towards the face and triggered accidentally, the jets will have no effect other than to shower the said face with active principle, without any mechanical piercing effect if the syringe is not in contact with (or very close to) the face. This advantage is associated with the control of the coherence distance of the jet.

The present invention will be described in greater detail with the aid of the following figures.

FIG. 2 depicts, in longitudinal section, details of a housing with the stack of plates of the previous example.

FIG. 3 depicts, in partial longitudinal section, the downstream end of a syringe in another exemplary embodiment.

FIG. 4 depicts, in longitudinal section, details of a housing with a stack of plates one of which constitutes a crossable membrane.

Figure 1:
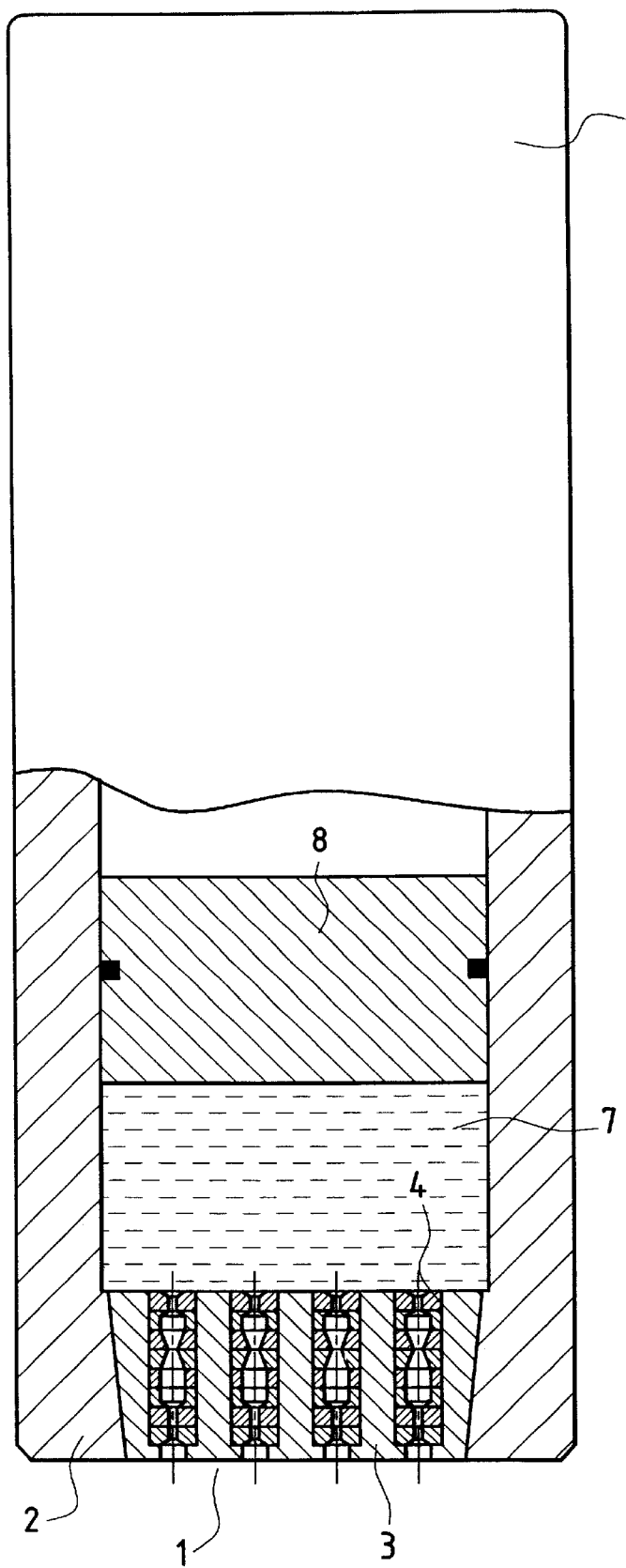
FIG. 1 depicts, in longitudinal part section, a syringe according to the invention; the injector of this syringe comprises several housings with identical stacks of plates each having a central orifice.

FIG. 1 schematically depicts a needleless syringe for injecting a liquid active principle. Such a syringe is generally cylindrical and comprises a reservoir containing the active principle 7. This reservoir is closed at one end, which we have termed the downstream end 2, by an injector 1 comprising at least one injection nozzle. This injector generally rests against the skin of the subject to be treated, or is held a very short distance away, the skin not being depicted in this drawing. This injector is the end of the reservoir or is an attached piece 3 fixed to this end of the reservoir by appropriate means. The other end of the reservoir is closed by a moveable wall, for example a piston 8 comprising sealing means such as an O-ring. Finally, the syringe comprises a propulsive system 9 with a triggering device for moving the piston and injecting the liquid. Among the propulsive systems that can be used, and without going into details thereof, mention will be made of a pyrotechnic gas generator as described in the previously-mentioned U.S. Pat. No. 3,802,430, mention will also be made of the expansion of a compressed gas or a compressed spring, as described in U.S. Pat. No. 3,788,315. Obviously, the syringes according to the invention may be equipped with one of these types of propulsive system in order to move the piston.

The support 3 of the injector 1 depicted in FIG. 1 is a frustoconical part forcibly fitted into the end 2 of the syringe. The support 3 comprises, in this example, eight identical housings arranged in two concentric circles, these housings 4 are cylindrical, open at their two ends, the opening of the downstream end having a smaller diameter so as to form a shoulder 31. In each housing 4 there is (see FIG. 2) an identical stack of eight plates (51, 61, 71, 81, 91, 51', 71', 91') all with the same outside diameter and the same thickness. Each plate has a central orifice of a simple shape: a cylinder of small diameter (plate 61), a cylinder of large diameter (plate 81), a cone frustum (plates 91 and 91', which differ through the orientation of the cone with respect to the flow of the liquid); a small cone frustum connected to a cylinder (plates 51 and 51'), a cone frustum connected to a cylinder (plates 71 and 71'). Stacking these plates in a particular order in a housing 4 produces a nozzle 50 of evolving cross section, the succession of the various cavities making it possible to control the coherence distance of the jet of liquid leaving this duct.

In this example, the plates have an outside diameter of about 3 mm and are about 1 mm thick. The orifices have a diameter between about 0.1 mm and about 0.6 mm. The support 3 has a diameter of about 20 mm to about 30 mm.

FIG. 3 depicts, in longitudinal section, the downstream end of another embodiment of a syringe according to the invention. In this embodiment, the support of the injector 10 is a shoulder 21 of the downstream end 20 of the syringe itself. Inside the single housing 40, which in this instance is cylindrical, of the end 20 of the syringe are stacked plates 52, 62, 72, 82 and 92 which are retained by the shoulder 21 of the end 20. The plates 62, 72, 82 and 92 are planar, with the same outside diameter, but different thicknesses. The most downstream plate 52 has a slightly more complex shape in that it has a downstream part centred in the opening of the shoulder 21 with a slightly convex downstream face; its opposite part has the same outside diameter as the other plates and is itself planar.

All the plates have the same number of orifices. These orifices have simple shapes in this example, namely cylinders and cone frustums. These shapes are combined to form nozzles of evolving cross-section. In this example, two types of nozzle 50, 60 are depicted. A device allows the plates to be orientated appropriately with respect to one another so as to produce the ducts. This device is a rib 41 belonging to the housing 40, engaging in a lateral notch of the various plates. The stack of plates 52, 62, 72, 82, 92 is forcibly fitted into the housing 40 of the end 20 of the syringe.

The materials for producing the syringe and the various parts of the injector will be chosen from materials which are compatible and approved for medical use; without claiming to be exhaustive, we quote by way of example, plastics materials such as polycarbonates, polytetrafluoroethylene; metals, such as stainless steels; or glass for medical use (for example type I or II).

FIG. 4 again shows a housing 4 similar to thee one described in FIG. 2. Stacked in this housing are perforated plates 53, 63, 73, 83 similar to those of the stack of FIG. 2 and a plate constituting a crossable membrane 100. In this example, the membrane 100 is produced from a thin sheet of a material which will tear when the liquid is pressurized at the time of injection. This membrane may also have a region of lesser thickness which will encourage the membrane to become pierced at this point, when the liquid is pressurized for injection. According to another alternative form, the membrane has pre-piercings which are aligned with the orifices in the plates 53, 63, 73, 83 and the elasticity of the material of the membrane keeps the pre-piercings closed when there is no pressure. The pressurizing of the liquid, for injection, causes the edges of the pre-piercings to part so as to allow the liquid through.

The crossable membrane is manufactured using an elastomer or polymer compatible with the liquid active principle; its thickness is between about 0.2 mm and about 1.5 mm.

What is claimed is:

1. A needleless syringe for injection, an active principle, the syringe comprising at its downstream end.

an injector with a support and having at least one injection nozzle;

the active principle; and a wall that can be displaced under the effect of a propulsive system, wherein the support comprises at least one housing in which substantially planar plates each having the same number of orifices are stacked, the orifices of the various plates being aligned to form the at least one injection nozzle that passe through the stack, and tile propulsive system pressurizes and expels the active principle through the at least one injection nozzle of the injector, and the orifices in the plates have simplest geometric shapes so to produce nozzles with evolving cross section.

2. The needleless syringe according to claim 3, wherein the housings and the plates comprise means of setting the angle of the plates in the corresponding housing.

3. The needleless syringe according to claim 2, wherein at least the most downstream plate is forcibly fitted into its housing.

4. The needleless syringe according to claim 2, wherein at least the most downstream plate is bonded into its housing.

5. The needleless syringe according to claim 1, wherein the support for the plates is the shoulder of the downstream end of the syringe.

6. The needleless syringe according to claim 1, wherein the said injector comprises at least one plate constituting a crossable membrane inserted between two consecutive plates.

7. An injector for a needleless syringe, the injector comprising a support, wherein the said support comprises at least one housing in which plates each having the same number of orifices stack, the said orifices being aligned to form at least one nozzle through the stack, and the orifices in the plates have simple geometric shapes so as to produce nozzles with evolving cross section.

8. A method of manufacturing an injector for a needleless syringe, comprising the following steps:

manufacturing a support comprising at least one housing, manufacturing plates all having, the same number of orifices, stacking and setting the substantially planar plates in a predetermined order in each housing to form at least one nozzle through the stack, wherein the orifices in the plates have simple geometric shapes so as to produce nozzles with evolving cross sections.

\* \* \* \* \*